United States Patent [19]

Gabourie

[11] Patent Number: 4,904,271

[45] Date of Patent: Feb. 27, 1990

[54] FINNED PHALANGEAL DEVICE

[75] Inventor: Robert Gabourie, St. Catharines, Canada

[73] Assignee: Niagara Prosthetics & Orthotics Corp., St. Catharines, Canada

[21] Appl. No.: 354,771

[22] Filed: May 22, 1989

[30] Foreign Application Priority Data

Feb. 21, 1989 [CA] Canada .................................. 591690

[51] Int. Cl.⁴ ................................................ A61F 2/00
[52] U.S. Cl. ........................................ 623/65; 441/57
[58] Field of Search .................................. 222/116, 71; 441/55–58; 434/254; 623/65

[56] References Cited

U.S. PATENT DOCUMENTS

| | | | |
|---|---|---|---|
| 1,004,394 | 9/1911 | Enders | 441/58 |
| 2,169,939 | 8/1939 | Anderson | 441/57 |
| 2,227,825 | 1/1941 | Devermann | 441/56 |
| 3,257,673 | 6/1966 | Rademacher | 441/57 |
| 4,548,588 | 10/1985 | Kosuge | 441/56 |

Primary Examiner—Richard J. Apley
Assistant Examiner—James Prizant

[57] ABSTRACT

A finned phalangeal device includes a plurality of spacially disposed, phalanges. On each phalange, a longitudinal flexible fin element is attached on the back side while allowing the longitudinal margins of each flexible film element to extend normally toward a like element on an adjacent phalange. When the device is moved in one direction through a fluid the flexible fin elements feather against the phalange and allow the fluid to pass between adjacent phalanges with relatively little resistance. When the device is moved in the opposite direction the flexible fin elements open to adjacently overlay each other and hence to provide a fluid seal inhibiting fluid flow between adjacent phalanges. In one embodiment the phalanges are integral members of a glove and specifically are finger encircling elements thereof while in another embodiment each phalange is a rigid prosthesis element simulating those fingers.

8 Claims, 2 Drawing Sheets

FINNED PHALANGEAL DEVICE

This invention relates to a prosthesis and particularly one which is adapted to be affixed to the end of one of the upper limbs such as, over the hand or as a replacement for a hand, or to the wrist.

Those who have lost a finger or fingers, or a hand, or have had an upper limb severed at or below the elbow have difficulty in swimming as there are insufficient or no fingers available to form a "web" and hence to provide the mechanical means for an efficient power stroke of the arm.

Swimming is an exercise that benefits ones health and is particularly helpful to handicapped persons and should be encouraged.

I have conceived of a fixture, which in one embodiment is in the form of a glove whose finger encircling elements have flexible lateral fin-like projections which when the palm of a hand is moved in a power stroke direction, against the water, the projections open to mate against adjacent projections and hence provide a web like seal to water thus converting the arm stroke into a power stroke for the swimmer.

In an alternative embodiment, the projections are affixed to each rigid phalange of a prosthesis which is structured in the form of a hand; the prosthesis having means for attaching the same to the wrist or upper arm.

In the power stroke, both embodiments operate the same. In the recovery stroke, the projections feather against the finger encircling elements of the glove or feather against the phalange of the prosthesis so as to allow easy movement through the water with little resistance.

In summary therefore, the invention has as an object, a finned phalangeal device includes a plurality of spacially disposed, phalanges. On each phalange, a longitudinal flexible fin element is attached on the back side while allowing the longitudinal margins of each flexible film element to extend normally toward a like element on an adjacent phalange. When the device is moved in one direction through a fluid the flexible fin elements feather against the phalange and allow the fluid to pass between adjacent phalanges with relatively little resistance. When the device is moved in the opposite direction the flexible fin elements open to adjacently overlay each other and hence to provide a fluid seal inhibiting fluid flow between adjacent phalanges. In one embodiment the phalanges are integral members of a glove and specifically are finger encircling elements thereof while in another embodiment each phalange is a rigid prosthesis element simulating those fingers.

The invention therefore contemplates a finned phalangeal device comprising:

(a) a plurality of spacially disposed phalanges that at one end merge into a body portion;

(b) attachment means defined by the body portion for attachment of the body portion to a protruding section of a human limb whereby to secure the device thereto; and, (c) a plurality of longitudinal flexible fin elements overlaying each phalange and having protruding longitudinal margins, the margins protruding beyond each phalange and adapted, to feather against the phalange when the device is moved through a liquid in one direction and hence to allow passage of the liquid between adjacent phalanges and when the device is moved through the liquid in the opposite direction to move into an extended and protruding position to make overlaying contact with the margin of an adjacent element so as to form a fluid barrier or seal between adjacent phalanges.

Additionally, the body portion may be a tubular overlay of the palm and back of the hand and each phalange an integral tubular finger engaging element so as to form a glove. In this embodiment, the glove can be a fabric or an elastomeric. The flexible fin elements can also be elastomeric.

In another embodiment, each phalangeal is a rigid longitudinal element that at one end extends into a rigid form body portion resembling that of a palm and having means for attachment to a severed upper limb.

The embodiments of the invention will now be described by way of example and reference the accompanying drawings in which.

Figure 1:
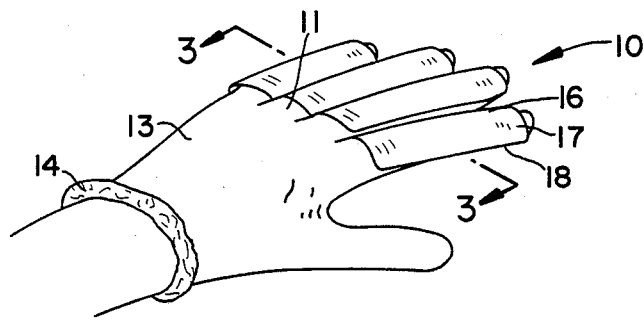
FIG. 1 illustrates a glove employing the fin-like projections on the fingers.

Referring to FIG. 1, a glove 10 is generally shown having finger encircling elements 11 integral to both the palm side 12 and the back of the hand side 13; the palm and back of the hand sides respectively are interjoined and terminate at a wrist-like cuff or wrist engagement means 14.

Each of the finger encircling elements 11 has along the upper back margin thereof and welded thereto at 16 a longitudinal sheet or fin member 17 with opposite flexible lateral margins 18.

Figures 3A, 3B:
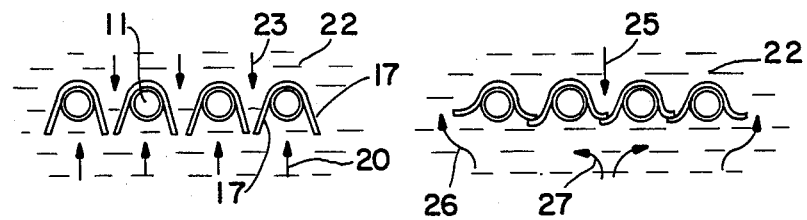
FIG. 3 is sectional view along III—III of FIG. 1.

Referring to FIGS. 3A and 3B, when the glove is moved backwards, during the recovery stroke in the direction of arrows 20, through water 22, the water travels in the direction of arrows 23 between the finger encircling elements 11 and causes each of the flexible fins 17 to feather into the position indicated in FIG. 3A.

Referring to FIG. 3B which is illustrative of the power stroke, when the glove 10, is moved by the hand, in direction 25, as during swimming and hence against the water 22, the water follows in the paths of arrows 26, and 27 and urges the fins 17, move from the feathered position shown in FIG. 3A to that of FIG. 3B so that the distal margins of adjacent fins overlap as shown. This provides resistance to the water and a power stroke can be initiated without the fingers being put together in a juxtaposed manner. Those who have arthritis in the hand will find such glove of use in swimming.

Figure 2:
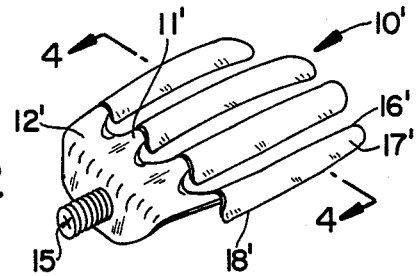
FIG. 2 is a perspective view of a prosthesis employing similar fins.
Figures 4A, 4B:
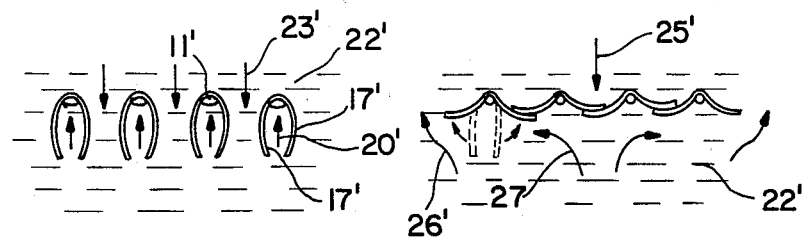
FIG. 4 is a sectional view along IV—IV of FIG. 2.
Figure 5:
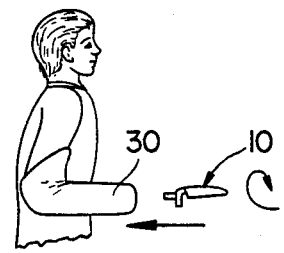
FIG. 5 illustrates the insertion of the prosthesis of FIG. 2 into the stump of a forearm.
Figure 6:
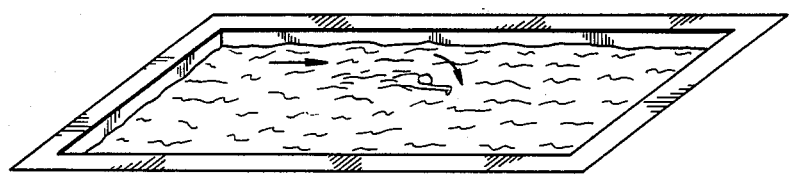
FIG. 6 is a perspective of a swimmer employing the prosthesis of FIGS. 1 or 2.

Referring now to FIGS. 2, 4A and 4B a prosthesis 10' is generally shown having fins 17' installed along phalanges 11', the phalanges merging into a base or palm piece 12' and terminating with a protruding stud 15 which, as seen in FIG. 5 is adapted, to be screwed into a forearm stump 30 that has a forward receiver, not shown, adapted to matingly engage with the threaded stud 15.

In a similar fashion and referring to FIGS. 4A and 4B, during the forward recovery stroke or movement of the prosthesis 10' as in FIG. 4A the fins 17 are feathered and water travels in the direction of arrow 23'. During the power stroke, adjacent fins move to overlap along there adjacent margins overlap, as shown in FIG. 4A, and the power stroke is initiated in the direction of arrow 25'.

I claim:

1. A finned phalangeal device comprising;
   (a) a plurality of spacially disposed phalanges that at one end merge into a body portion;
   (b) attachment means defined by the body portion for attachment of the body portion to a protruding section of a human limb whereby to secure the device thereto; and,
   (c) a plurality of longitudinal flexible fin elements overlaying each phalange and having protruding longitudinal margins, the margins protruding beyond each phalange and adapted, to feather against the phalange when the device is moved through a liquid in one direction and hence to allow passage of the liquid between adjacent phalanges and when the device is moved through the liquid in the opposite direction to move into an extended and protruding position to make overlaying contact with the margin of an adjacent element so as to form a fluid barrier or seal between adjacent phalange.

2. The device claimed in claim 1 wherein each flexible film element is elastameric.

3. The device claimed in claim 2 wherein the body portion is a tubular portion that is adapted to overlay the palm and the back of the hand, and each phalange is a tubular finger engaging element.

4. The device claimed in claim 1 wherein each phalange is a rigid longitudinal element that at one end extends into a rigid formed body portion, the body portion carrying said attachment means (b).

5. The device claimed in claim 2 wherein each phalange is a rigid longitudinal element that at one end extends into a rigid formed body portion, the body portion carrying said attachment means (b).

6. The device claimed in claim 1 wherein each phalange is a rigid longitudinal element that at one end extends into a rigid formed body portion, the body portion carrying said attachment means (b) wherein the attachment means is a threaded stud.

7. The device claimed in claim 2 wherein each phalange is a rigid longitudinal element that at one end extends into a rigid formed body portion, the body portion carrying said attachment means (b) wherein the attachment means is a threaded stud.

8. The device as claimed in claim 3 wherein the attachment means is a wrist engaging cuff.

* * * * *